United States Patent [19]

Pisharodi

[11] Patent Number: 5,390,683
[45] Date of Patent: Feb. 21, 1995

[54] SPINAL IMPLANTATION METHODS UTILIZING A MIDDLE EXPANDABLE IMPLANT

[76] Inventor: Madhavan Pisharodi, 844 Central Blvd., Suite 1200, Brownsville, Tex. 78520

[21] Appl. No.: 107,750
[22] PCT Filed: Feb. 21, 1992
[86] PCT No.: PCT/US92/01397
 § 371 Date: Aug. 20, 1993
 § 102(e) Date: Aug. 20, 1993
[87] PCT Pub. No.: WO92/14423
 PCT Pub. Date: Sep. 3, 1992

Related U.S. Application Data

[63] Continuation-in-part of Ser. No. 106,148, Aug. 13, 1993, abandoned, which is a continuation of Ser. No. 786,758, Nov. 1, 1991, abandoned, which is a continuation-in-part of Ser. No. 659,758, Feb. 22, 1991, Pat. No. 5,171,278.

[51] Int. Cl.$^6$ .......................... A61B 19/00; A61F 2/44
[52] U.S. Cl. ........................ 128/898; 623/17; 606/61; 128/899
[58] Field of Search ................... 128/897–899; 606/60–75; 623/17; 602/5, 12, 18, 19, 20, 23, 32, 36

[56] References Cited

U.S. PATENT DOCUMENTS

| | | |
|---|---|---|
| 725,874 | 4/1903 | Riley . |
| 2,226,078 | 12/1940 | Spahn . |
| 3,030,903 | 4/1962 | Morris . |
| 3,867,728 | 2/1975 | Stubstad et al. . |
| 3,986,383 | 10/1976 | Petteys . |
| 4,309,777 | 1/1982 | Patil . |
| 4,401,112 | 8/1983 | Rezaian . |
| 4,465,220 | 8/1984 | Ledlow et al. . |
| 4,553,273 | 11/1985 | Wu .................................. 623/18 |
| 4,657,550 | 4/1987 | Daher . |
| 4,759,769 | 7/1988 | Hedman et al. . |
| 4,772,287 | 9/1988 | Ray et al. ......................... 623/17 |
| 4,834,757 | 5/1989 | Brantigan . |
| 4,863,476 | 9/1989 | Shepperd . |
| 4,863,477 | 9/1989 | Monson . |
| 4,904,260 | 2/1990 | Ray et al. . |
| 4,904,264 | 2/1990 | Scheunemann . |
| 4,932,969 | 6/1990 | Frey et al. . |
| 4,932,975 | 6/1990 | Main et al. . |
| 5,002,576 | 3/1991 | Fuhrmann et al. . |
| 5,059,193 | 10/1991 | Kuslich ............................ 606/61 |
| 5,171,278 | 12/1992 | Pisharodi . |

FOREIGN PATENT DOCUMENTS

| | | |
|---|---|---|
| 0260044 | 3/1988 | European Pat. Off. . |
| 304305A | 2/1989 | European Pat. Off. . |
| 2639823 | 6/1990 | France . |
| 38822 | 8/1965 | Germany . |
| 3729600 | 3/1989 | Germany . |
| 1124955 | 11/1984 | U.S.S.R. . |

Primary Examiner—Angela D. Sykes
Assistant Examiner—J. P. Lacyk
Attorney, Agent, or Firm—Vaden, Eickenroht, Thompson, Boulware & Feather

[57] ABSTRACT

Artificial disk implant and methods for implanting same, the implant having a member (32, 34, 36, 77, 92, 94) for adapting in size and shape to the anatomical space between vertebrae, and apparatus (25, 42, 60, 112) for expanding the implant in the middle portion thereof to conform to the space. In one embodiment, there is provided an artificial intervertebral disk implant having a cylindrical body (20, 41, 56, 88) comprised of cylindrical subunits (32, 34, 36, 92, 94) capable of expansion. In another embodiment, rectangular members (34, 36) or elongate ribs (77) capable of expansion are provided. The implant can be used alone or in various combinations for the purpose of spinal fusion.

11 Claims, 4 Drawing Sheets

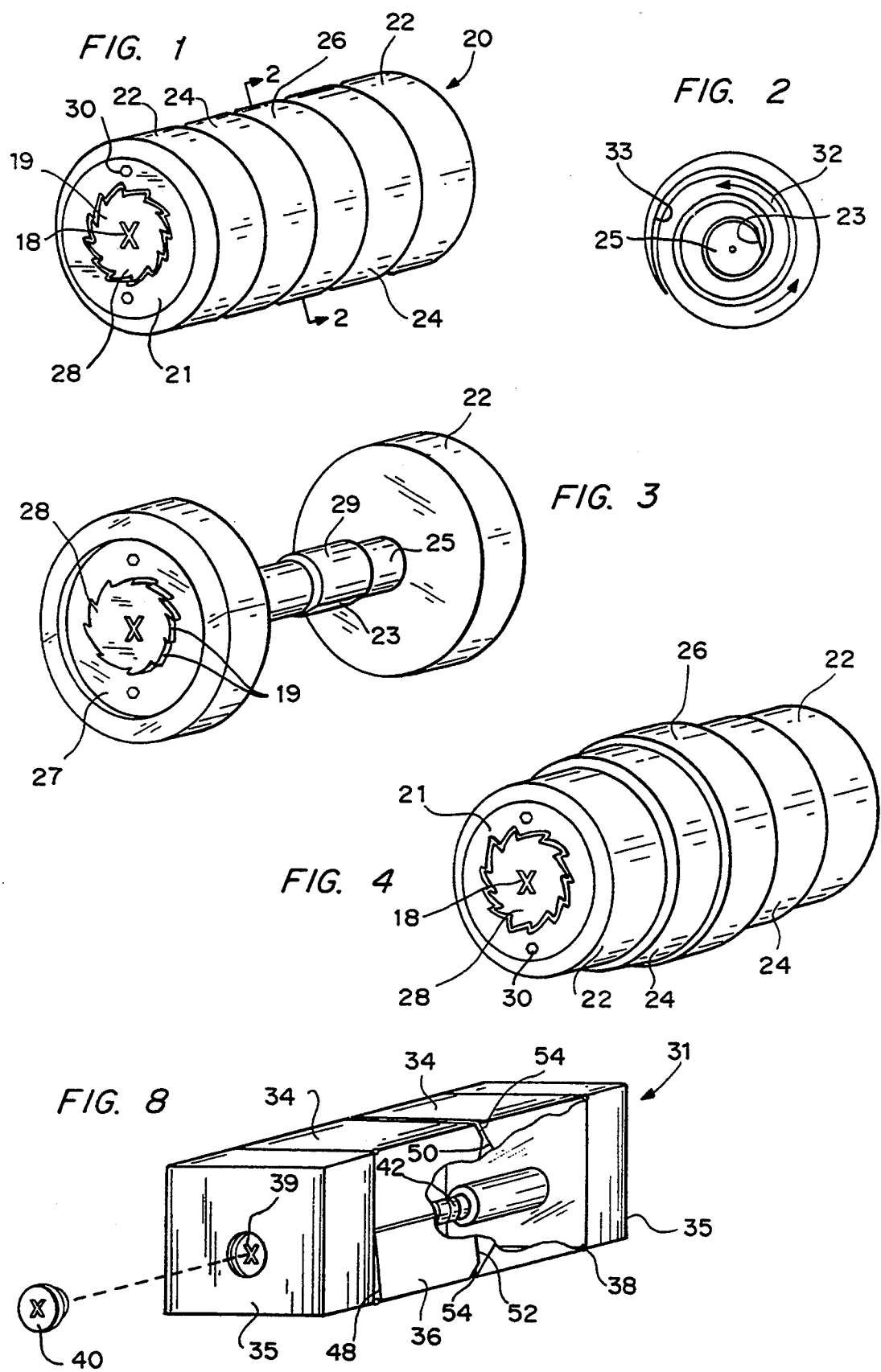

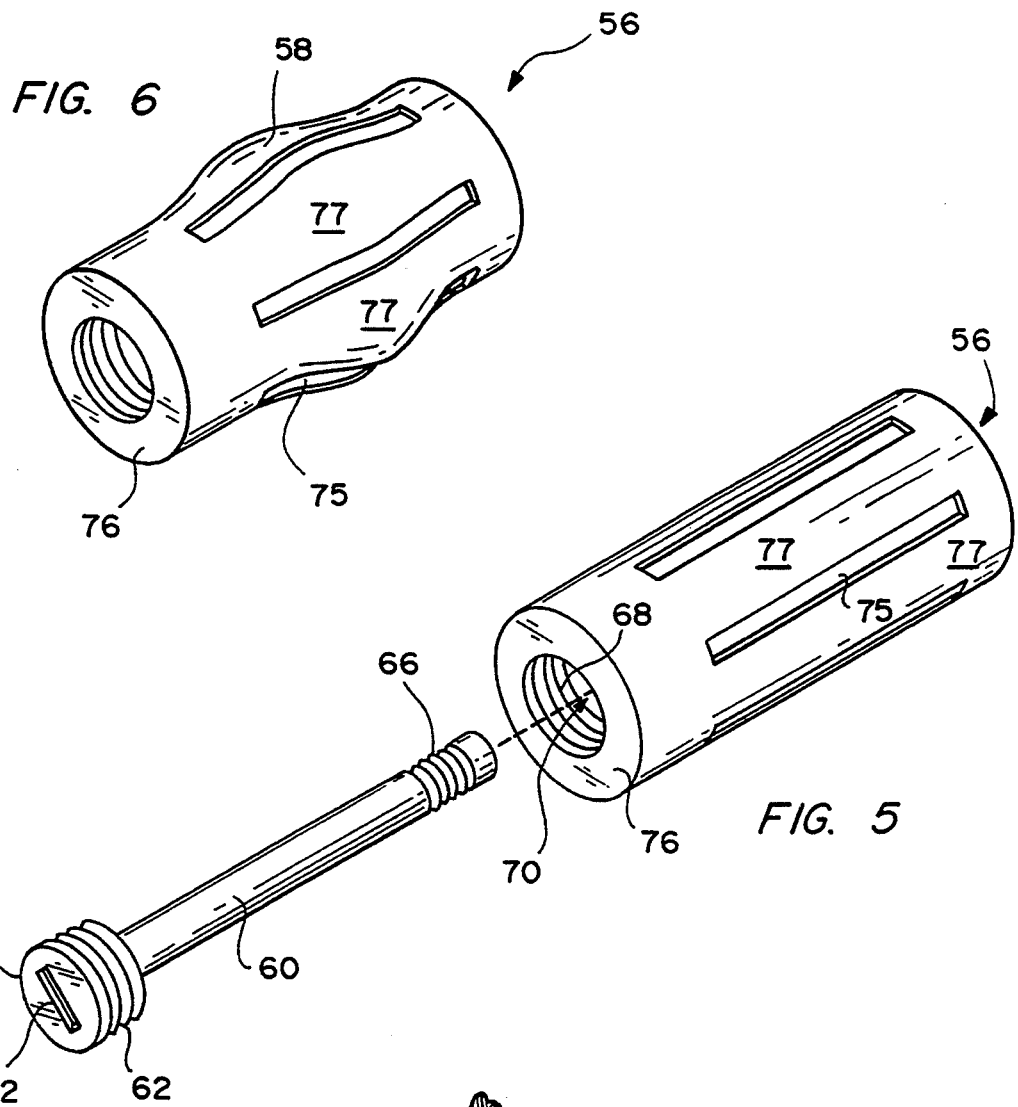
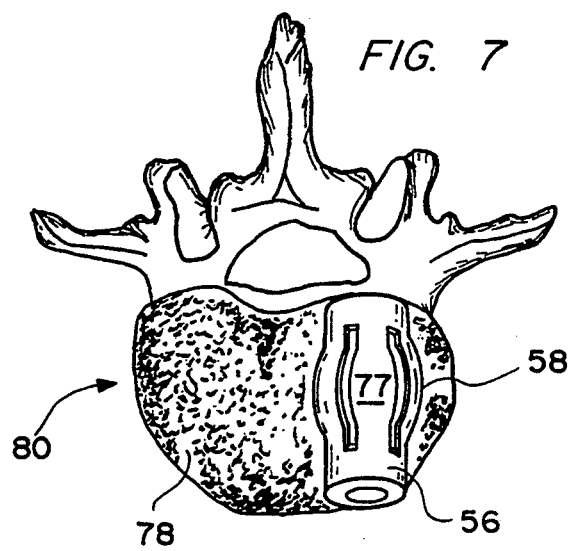

SPINAL IMPLANTATION METHODS UTILIZING A MIDDLE EXPANDABLE IMPLANT

This application is a continuation-in-part of my application Ser. No. 08/106,148, filed on Aug. 13, 1993, now abandoned. Ser. No. 08/106,148, was filed as a continuation application of application Ser. No. 07/786,758, which was filed on Nov. 1, 1991, and is now abandoned, Ser. No. 07/786,758, having been itself filed as a continuation-in-part of application Ser. No. 07/659,758, filed on Feb. 22, 1991, now issued as U.S. Pat. No. 5,171,278.

BACKGROUND OF THE INVENTION

This invention relates to an intervertebral disk implant and a method of implanting same. More specifically, the present invention relates to cylindrical and rectangular disk implants which are expandable in the middle portion which are used alone or in various combinations for the purpose of spinal fusion.

The spine is a flexible structure comprised of thirty-three vertebrae separated and cushioned from each other by fibrous intervertebral disks. If the spine is injured or becomes diseased, surgical intervention involving removal of one or more disks, and fusion of the adjacent vertebrae, may be indicated. The more frequent injuries are in the lower lumbar and in the lower cervical regions.

Treatment of a herniated disk in the neck and in the lumbar region continues to be a challenging field of medicine. The classical treatment for a ruptured disk continues to be diskectomy, i.e., removal of the disk from between the vertebrae. In this process, all or a portion of the intervertebral disk is removed, leaving a defect which continues to bother the patients throughout the rest of their lives. An additional procedure is to replace the disk space with a bone graft, usually bone chips cut from the patient's iliac crest, bringing about fusion of the vertebrae above and below the disk, eliminating the empty space between the vertebrae.

Theoretically, a diskectomy with fusion is a satisfactory procedure, though not ideal because the replaced bone does not have any of the functions of the cartilage tissue of the disk, i.e. no cushioning effect, and has complications because of several factors. First, the bone plug used to pack the disk space does not conform to the shape of the disk because the disk bulges maximally in the center. The disk space is wider in the middle and narrower at its anterior and posterior ends. Consequently, a bone plug having its maximum width at the center, e.g., one which is shaped to fit the space, cannot be inserted through the narrow mouth of the disk space. For this reason, the various bone plugs which are currently available commercially have only four contact points, i.e. at the front and back of the disk space. Secondly, access to the disk is from one side or the other of the dorsal spine of the adjacent vertebrae, leaving a space that is "off-center" relative to the bodies of the adjacent vertebrae. An implant inserted into that off-center space, therefore, replaces only a portion of the disk and consequently contacts only a portion of the bodies of the adjacent vertebrae such that the stability of the implant is even more problematical than might be apparent from the limited contact resulting from the shape of the intervertebral space in the first place. Another complication is the possibility of infection or other conditions which may require the removal of the implant. Also, if the bone pieces do not fuse, they may eventually extrude out of the disk space, causing pressure on the nerve roots.

Various prosthetic disk plugs, or implants, are disclosed in the art, but all are characterized by limitations of not conforming to the shape of the disk space, lack of stability when inserted off-center, inability to be removed, or other disadvantages. For instance, U.S. Pat. No. 4,863,476 describes an elongated body divided longitudinally into two portions having a cam device movable therebetween for increasing the space between the two body portions. However, that device is generally cylindrical in shape such that the only contact points are at the front and back of the disk space, creating increased likelihood of instability and generally rendering that device unsuitable for use after partial diskectomy. The art also discloses intervertebral disk prostheses (e.g., U.S. Pat. Nos. 3,867,728, 4,309,777, 4,863,477 and 4,932,969 and French Patent Application No. 8816184) which may have more general contact with the adjacent disks, but which are not intended for use in fusion of the disks. The art also includes spinal joint prostheses such as is described in U.S. Pat. No. 4,759,769, which is again not indicated for use when fusion is the preferred surgical intervention.

From this prior art, it is apparent that there has long been a need for a disk plug, or implant, capable of supporting the disk space after a simple diskectomy for fusion of adjacent vertebrae, and the object of the present invention is to provide such an implant.

SUMMARY OF THE INVENTION

An intervertebral disk implant is described for implantation into the disk space after surgical removal of all or a portion of a diseased or damaged disk. Implants according to this invention include means for changing the shape of the implant to adapt to the shape of the disk space by expanding the implant to conform to the contour of that space, and are, for that reason, referred to herein as being "middle expandable".

In one embodiment, there is provided an intervertebral disk implant with a cylindrical body comprised of subunits capable of radially outward expansion. In another embodiment, there is provided an implant having a substantially rectangular body likewise comprised of subunits capable of radially outward expansion. Both are disk plugs expandable in the middle portion to provide contact with substantially the entire area of the disk space against the vertebral bodies.

In the method of the present invention, there is provided a method of fusing two adjacent vertebrae after removal of all or a portion of the disk from therebetween which comprises inserting a disk implant into the space from which the disk has been removed, expanding the middle portion of the implant outwardly in a radial direction, injecting cancellous bone chips into the disk space medial to the implant, and applying a physiologically compatible adhesive over the bone chips medial to the implant to close off the opening of the disk space.

BRIEF DESCRIPTION OF THE DRAWINGS

In the drawings, FIG. 1 is a projected view of one embodiment of the disk implant of the present invention.

FIG. 2 is a cross sectional view of the disk implant of FIG. 1 taken along the line 2—2 in FIG. 1.

FIG. 3 is a projected view of the central axis of the disk implant of FIG. 1 having the members coiled therearound removed therefrom.

FIG. 4 is a projected view of the implant of FIG. 1 after expansion of the middle portion thereof.

FIG. 5 is a projected, exploded view of a second embodiment of the disk implant of the present invention.

FIG. 6 is a projected view of the implant of FIG. 5 showing that implant after expansion thereof.

FIG. 7 is a top, plan view of a lumbar vertebra of a human patient having a top, plan view of the implant of FIG. 6 superimposed thereon to show the spatial relationship of the implant to the adjacent vertebrae after insertion into the disk space.

FIG. 8 is a projected view of another embodiment of the implant of the present invention.

DETAILED DESCRIPTION OF THE INVENTION

Figure 9:
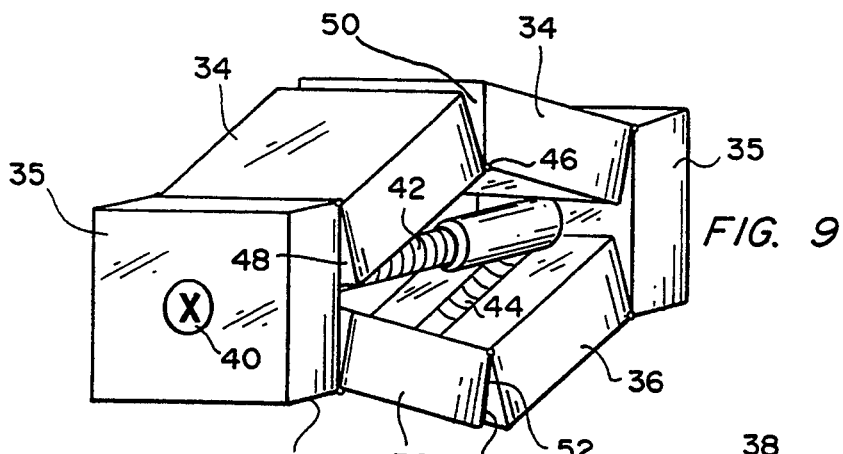
FIG. 9 is a projected view of the disk implant of FIG. 8 after expansion of the middle portion thereof.

FIG. 1 depicts a cylindrical embodiment of the disk implant of the present invention. The disk implant 20 shown in that figure is comprised of a strong, thin nonporous material. Suitable materials for the disk implant 20 include modified carbon, titanium, steel, metals and/or metal alloys having a memory (see below), physiologically inert and/or medically compatible polymers such as a urethane or DELRIN® polymer, or any generally rigid, biologically compatible material used for surgical implants. It is also useful to use a material which is compatible with magnetic resonance imaging (MRI) procedures. The disk implant 20 is comprised of a plurality of longitudinally aligned sections, or subunits 22, 24 and 26, and a screw 28 to which each section is mounted (as described below) is turned to cause differential, radially outward expansion of subunits 24 and 26. The subunits 24 and 26 are preferably comprised of a material capable of maintaining spring tension and are mounted to and wound around an elongate longitudinal axis in the form of central rod 25 (see FIGS. 2 and 3) integral with screwhead 28. Because of this structure, each of the subunits is conveniently referred to as including a coiled member as identified at reference numeral 32.

Each coiled member 32 is mounted to central rod 25 by welding, riveting, or by other manner depending upon the material(s) comprising the sheet 32 and central rod 25 as known in the art. In the preferred embodiment shown in FIGS. 1-4, the central rod 25 is provided with a flat 23 to provide a stable surface for mounting of the member 32 thereto by, for instance, welding. At the other, free end of each coiled member 32, the coiled member 32 is beveled as at reference numeral 33 so as to provide a smooth, generally round exterior surface on each of the subunits 24 and 26 and to facilitate the sliding of the free end of coiled member 32 along the outside surface thereof as the subunits 24 and 26 are expanded radially outwardly as described below.

A Phillips head-type slot 18 is provided in the screwhead 28 for rotation of the rod 25 as described below, and the head 28 is provided with a plurality of teeth 19 for interdigitating with the reciprocal cavities in the lock nut 21 to prevent undesired rotation of central rod 25. The Allen screws 30 are loosened to force lock nut 21 away from the end surface 27 of subunit 22 so that the teeth 19 on the head 28 of central rod 25 are disengaged from the cavities in lock nut 21 to allow rotation of screwhead 28 and rod 25. Alternatively, either or both of rod 25 or lock nut 21 is comprised of a resilient, medically compatible polymer material which allows rotation of the teeth 19 past the cavities in lock nut 21 in one direction but not the other. The expanded shape of a section of the disk implant 20 is shown in FIG. 2.

Turning screwhead 28 and central rod 25 using the slot 18 expands the sections 24 and 26, which remain expanded due to the interaction of the teeth 19 and the cavities in lock nut 21 and the compression of the implant 20 between the bodies of the vertebrae above and below the implant 20 once inserted into the disk space. In other words, engagement of the free end of coiled member 32 by the adjacent vertebrae prevents the slipping of the free end of the coiled member 32 around the outside circumference of implant 20 such that members 32 do not "re-wind" after being expanded.

As shown in FIG. 3, central rod 25 is provided with a portion 29 approximately mid-way between the ends thereof having a larger diameter than the rest of the central rod 25. By use of the central rod with sections of different diameters and/or thicknesses of the cylindrically wound member 32, the subunits 24 and 26 are differentially expanded. Turning screw 28 allows for maximal expansion of the subunit 26 and moderate expansion of the subunit 24 because the member 32 comprising subunit 26 is mounted to the rod 25 on the portion 29 of larger diameter while each of the members 32 comprising subunits 22 and 24 is mounted to central rod 25 between the portion 29 and the subunits 22. Turning the central rod 25 uncoils the members 32 because each member 32 is attached to the central rod 25.

FIG. 4 illustrates the cylindrical disk implant 20 in its radially expanded form. Once expanded, the implant cannot be removed from the disk space except by turning the allen screws 30 to either back out or remove lock nut 21, thereby allowing rotation of rod 25.

Referring now to FIGS. 5 and 6, an alternative embodiment of the implant 20 is shown at reference numeral 56. Implant 56 is comprised of a single piece of metal, such as a titanium alloy, or medical grade polymeric plastic, such as DELRIN®, which is resilient and has a memory for the shape in which it is molded, shown in FIG. 6. Implant 56 is molded in the same generally elongate, cylindrical shape as the implant 20 shown in FIGS. 1-4, but is molded in a shape in which the middle portion 58 thereof is normally expanded radially outwardly from the central axis of the cylinder. An elongate screw 60 is provided having two sets of threads 62 and 66 thereon, the former for engaging the threads 68 formed in the bore 70 extending longitudinally through implant 56, the latter for engaging a similarly formed set of threads located in the bore 70 at the other end of implant 56 and therefore not visible in FIGS. 5 and 6. A slot 72 is formed in the head 74 of screw 60 for turning screw 60 to move the opposite ends 76a and 76b of implant 56 away from each other, thereby extending implant 56 and decreasing the radially outward expansion of the middle 58 thereof as shown in FIG. 5 for insertion into the disk space. Longitudinal slots 75 are molded into implant 56 to form ribs 77 which flex to allow the extension and outward expansion of implant 56 in this manner.

As noted above, the instability of prior implants once inserted into the disk space is problematical, and FIG. 7, showing the implant 56 in place relative to the body 78 of an adjacent lumbar vertebra 80 illustrates how the apparatus of the present invention overcomes this limitation of prior implants. The implant 56 is inserted into the disk space in an anterior-posterior (A-P) orientation, the dorsal spine 82 of vertebra 80 being pointed posterially. As clearly shown in FIG. 7, when so positioned, implant 56 occupies only a portion of the surface area of the vertebral body 78, the remainder of the area being occupied by that portion of the intervertebral disk (not shown) which is not removed during the diskectomy procedure (or, in a fusion procedure, this area is packed with cancellous bone chips). Access to that area is from the posterior aspect of the disk medial to the implant. In addition, the periphery 88 of vertebral body 78 is, as described above, thicker than the central portion 90 of body 78, further limiting access and creating an uneven surface on which the body 78 bears on the implant. However, because of the expansion of only the middle 58 of implant 56, the implant 56 is stable in the A-P orientation shown. Once implanted, the screw 60 is backed out of the bore 70 in implant 56 and implant 56 assumes the shape shown in FIGS. 6 and 7.

FIG. 8 depicts a rectangular disk implant 31 constructed according to the present invention. Turning Phillips head 39 of screw 42 encapsulated in a sheath 44 (best shown in FIG. 9) formed in the hinged members 34 and 36 forming intermediate subunits in the same manner as the subunits, or sections, 24 and 26 of implant 20 causes the radially outward expansion of superior hinged members 34 superiorly and inferior hinged members 36 inferiorly. Although shown in FIGS. 8 and 9 with two of the hinged members 34 and 36, it will be understood by those skilled in the art who have the benefit of this disclosure that the plug, or implant, 31 may be provided with four, eight, or even more of the hinged members 34 and 36 as shown at reference numerals 92 and 94 in FIG. 10 and numeral 41 in FIGS. 11–13. The expanded shape of the rectangular disk plug 31 is illustrated in FIG. 9. Hinged members 34 and 36 are secured to an end cap or subunit 33 by hinge 38 and to each other by hinge 46. Upon rotation of screw 42 using a conventional screwdriver and the Phillips head slot 39, the end caps 33 are drawn closer together by movement along the threads of screw 42. To insure that the members 34 and 36 expand radially outwardly from screw 42, the ends 48 of each respective member 34 and 36 abutting the end caps 33 are angled so as to create a force vector outwardly away from screw 42 when end cap 33 exerts pressure on the surface 48, the hinge 38 being mounted in the acute angle formed by surface 48 and end cap 33.

In one embodiment (best shown in FIGS. 11–13 and discussed below), the tendency of this force vector to cause the members 34 and 36 to expand is increased by angling the face 50 of one member 34 or 36 in the same direction as the angle in the surface 48. The surface 52 of the opposed member 34 and 36 is similarly angled, but with a bearing surface 54 formed therein that is angled in the same direction as the angle in surface 48 and face 50 so that the face 50 rides upwardly onto bearing surface 54 to translate the opposed, end-to-end force vectors applied to end caps 33 by rotation of screw 42 into a force vector having a radially outward (from screw 42) component. By referring to FIGS. 11–13, it can be seen that the radially outward expansion of the middle portion of implant 31 caused by rotation of the screw 42 effectively simulates the opening of two opposed umbrellas, and the particular embodiment shown in those figures may be conveniently referred to as having a "double umbrella" configuration.

A threaded lock nut 40 is inserted over Phillips screw head 39 (see FIG. 8). Lock nut 40 prevents the members 34 and 36 from moving once expanded. Removing lock nut 40 provides access to screw head 39 to allow members 34 and 36 to return to the position shown in FIG. 8.

Figure 10:
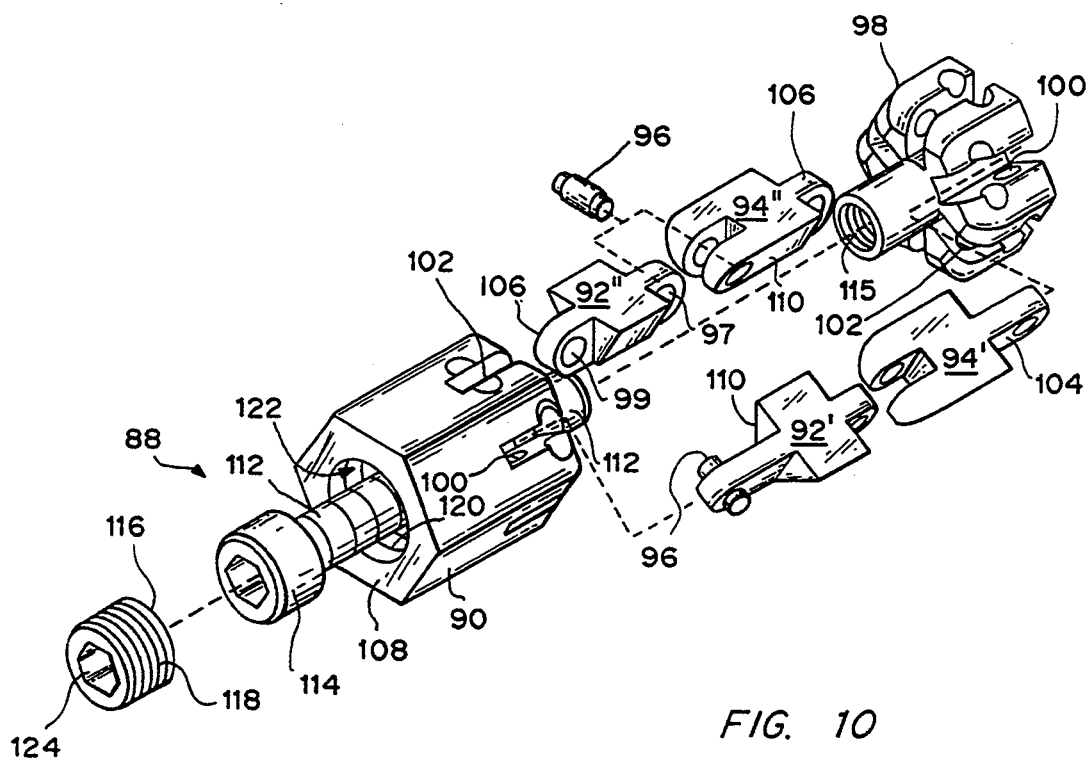
FIG. 10 is an exploded, projected view of a fourth embodiment of the implant of the present invention.

The above-referenced, double-umbrella configuration of the implant of the present invention is illustrated at reference numeral 88 in FIG. 10. In this embodiment, the hinged members 92 and 94 are mounted on pivot pins 96 to the first and second end members 90 and 98, respectively, as well as to each other, most of the pins 96 and all but two sets of the hinged members 92 and 94 being omitted from the figure for purposes of clarity. The pivot pins 96 which mount members 92 and 94 to the ends 90 and 98 are received within the bores 100 and 102 formed in each end member 90 and 98, the bores 100 and 102 being numbered separately to draw attention to their arrangement on the end members 90 and 98. The ears 104 on hinged members 92' and 94' are longer than the ears 106 on hinged members 92" and 94" and the bores 100 for receiving the pivot pin 96 are located closer to the end surface 108 of end member 90 (and the corresponding end surface of end member 98 at the opposite end of implant 88) than the bores 102. By this arrangement, the strength of the implant 88 is significantly increased.

Figure 10A:
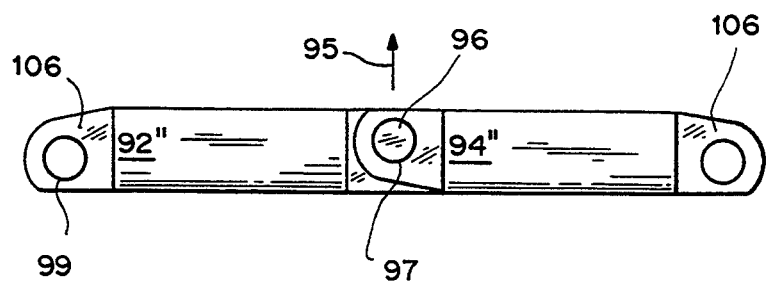
FIG. 10A is a side view of two hinged members comprising the middle portion of the implant of FIG. 10 and removed therefrom.

Expansion of the middle portion of implant 88 is accomplished by turning the screw 112 using the hex head 114 formed at one end thereof, the other end of screw 112 being received by the threads 115 formed in the second end member 98. To increase the tendency of the hinged members 92 and 94 to expand in the radially outward direction, the holes in the hinged members 92 and 94 in which pivot pins 96 reside are offset along the longitudinal axis of implant 88. The offset holes are better shown in FIG. 10A in which one pair of the members 92 and 94 is shown in side view removed from implant 88. The direction of expansion is shown by the arrow 95 in FIG. 10A and, as can be seen, the center holes 97 are offset outwardly (e.g., in the direction of arrow 95) relative to the holes 99 at the ends of hinged members 92 and 94 (e.g., in the ears 106).

A lock nut 116 having threads 118 formed in the outside surface thereof is received by the threads 120 formed in the bore 122 in end member 90 through which the screw 112 is received for preventing undesired rotation of screw 112. Lock nut 116 is provided with a hex slot 124 to facilitate insertion and/or removal and hex slot 124 extends all the way through lock nut 116 and is of large enough size that a hex key can be inserted through slot 124 and into hex head 114 for turning screw 112 without adjustment of lock nut 116.

Figure 11:
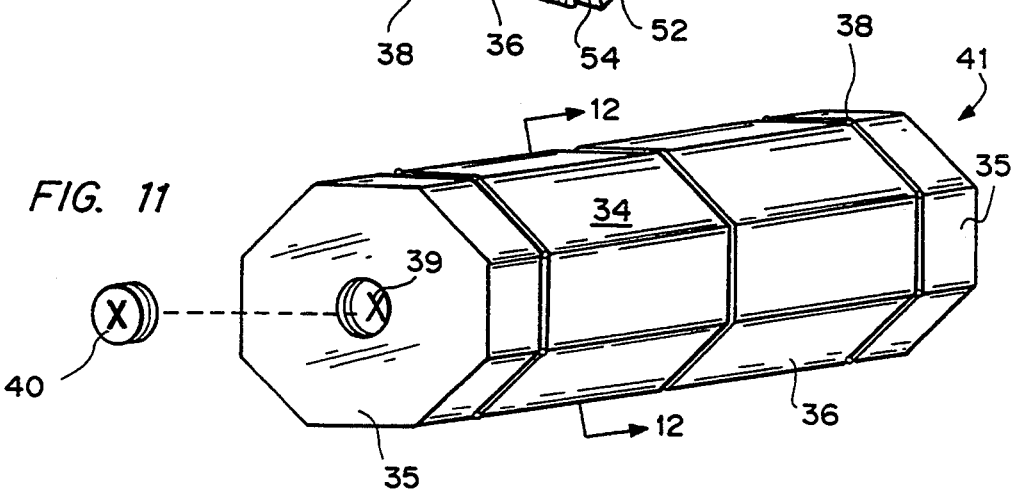
FIG. 11 is a projected view of a fifth embodiment of the disk implant of the present application.
Figure 12:
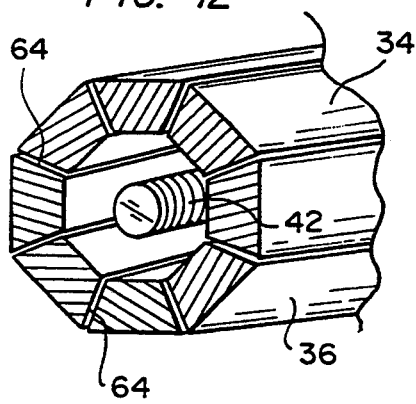
FIG. 12 is a cross sectional view of the disk implant of FIG. 11 taken along the line 12—12 in FIG. 11.
Figure 13:
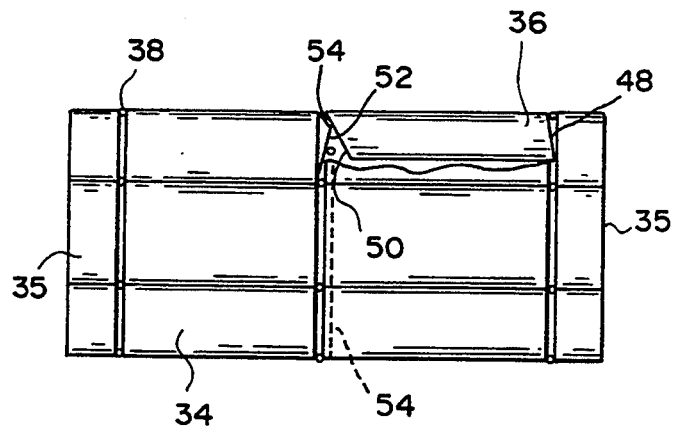
FIG. 13 is a side view of the disk implant of FIG. 11 showing a portion broken away therefrom.

Another embodiment of the double-umbrella configuration of the implant of the present invention is shown at reference numeral 41 in FIGS. 11–13. As is the case with the implant 88 shown in FIG. 10, the implant 41 is generally cylindrical in shape, yet utilizes the hinged member 34 and 36 construction of implant 31 shown in FIGS. 8 and 9. FIG. 12 shows a projected view of the disk implant 41 shown in FIG. 11 having the members 34 and 36 cut in section. This view shows how the hinged members 34 and 36 fit together in the unexpanded position due to their beveled sides 64, giving the implant 41 its generally cylindrical shape. The sides 110 of the hinged members 92 and 94 of implant 88 are similarly beveled (FIG. 10).

All of the disk implants of the present invention are expandable in the middle portion, i.e., the portion intermediate the ends, to contact substantially the entire anterior-posterior dimension of the disk space against the vertebral bodies as described above in connection with the description of FIG. 7. If a complete intervertebral fusion is being performed, the plug is used in conjunction with intervertebral cancellous bone packing. Because of the support provided by the plug, until fusion is established, the cancellous bone pieces have a better chance of fusion due to the presence of the implant, and the bone pieces and the disk implant have a better chance of staying in the intervertebral disk space. Alternatively, the plug is used to maintain the spacing between vertebrae and can be used in conjunction with intertransverse posterior lateral fusion. In short, the implant acts as a physiological support for the rest of the patient's life or until a bone fusion is established.

The disk implant of the present invention may have additional indications, e.g. short segment scoliosis, where the curvature of the spine can be corrected by distracting the vertebral bodies on the inside of the curvature. By expanding the middle portion of the plug inside the disk space, the vertebral bodies are distracted, thereby helping straighten the spinal column.

If no bone graft is planned, diskectomy can be made minimally through one side exposure so that when the disk plug is inserted and expanded, it will occupy the empty space. Because there is no further movement at this disk space, the chance of recurrent disk herniation is minimized. Also, the likelihood of recurrent disk herniation due to opening and closing of the space on the side of the diskectomy is reduced because the disk plug closes this mouth. Consequently, in addition to the advantages of a one sided, simple diskectomy, the risk of recurrent disk herniation can be reduced.

The cylindrical 20, 41, 56, and 88 and rectangular 31 implants are inserted after a simple diskectomy. Ordinarily, the size of the disk implant is approximately 2.5 to 3.5 centimeters in length and 1.0 to 1.5 centimeters in height and width. The same plug in smaller dimensions is used in thoracic and cervical levels where indicated.

By reference to the figures, it can be seen that both the rectangular and the cylindrical implants have the common feature of being expandable in the middle without changing the diameter of the dimensions of the two ends. Consequently, surgery is performed as in simple diskectomy, and the disk is exposed through a small laminotomy. The disk material is removed and any nerve root compression is corrected. The posterior longitudinal ligament and disk cartilage are removed until the vertebral surfaces are exposed above and below the disk space. The shape of the disk space determines whether the disk plug used is cylindrical or rectangular. The disk plug is then inserted and hammered into place so that the anterior end of the disk plug almost touches the anterior longitudinal ligament. Subsequently, using a Phillips screwdriver, the posterior screw end is turned. This implant method also gives good distraction to the vertebral bodies. In the case of simple disk problems, no further treatment may be required.

When used in interbody fusion, cancellous bone chips are made into very fine particles and pumped into the disk space medial to the disk plug and packed into the space. The posterior longitudinal ligament is intact to the opposite side and to the center of the disk space. These cancellous bone chips are held tightly in place. Since the mouth of the disk space is closed with the disk plug, the risk of the cancellous bone chips coming out is minimized. Also, the disk plug prevents the opening and closing of the disk space, thus preventing the bone chips coming out. If necessary, a small amount of a physiologically compatible adhesive of a type known in the art is applied over the cancellous bone chips just medial to the disk plug to close off the remaining portion of the opening of the disk space. The patient should be able to ambulate soon after the surgery because of the stability given by the disk plug. Before narrowing of the disk space occurs, the cancellous bone chips will have started the fusion process.

If a posterior lateral intertransverse fusion is desired, this procedure is also done in conjunction with the middle expandable disk plug. The disk plug is applied as explained above and the posterior lateral fusion performed. Since the disk plug provides stability to the spine until the posterior lateral fusion is solid, the patient can ambulate soon after the surgery. This procedure also prevents the disk space narrowing, which is a common problem with posterior lateral fusion.

What is claimed is:

1. A method of maintaining the space between two adjacent vertebrae of a patient after removal of the disk from therebetween comprising the steps of:

inserting an elongate implant comprised of a central rod having two ends and an intermediate portion mounted thereto into the space between two vertebrae after removal of the disk therefrom, the implant having a length which approximates the anterior-posterior dimension of the body of the vertebrae and a vertical dimension small enough to allow the insertion of the implant;

rotating the central rod to expand the intermediate portion of the implant radially outwardly to conform the shape of the implant to the shape of the anatomical region of the disk space into which the implant is inserted; and preventing the rotation of the central rod to prevent reversal of the outward radial expansion of the intermediate portion of the implant.

2. A method of claim 1 further comprising injecting cancellous bone chips into said disk space medial to the implant.

3. A method for fusing two adjacent vertebrae after removal of a portion of the disk from therebetween comprising the steps of:

inserting an elongate implant through an opening into a space between two adjacent vertebrae of a patient after removal of the disk from between the vertebrae, the implant having a length which approximates the anterior-posterior dimension of the body of the vertebrae and a vertical dimension small enough to allow insertion of the implant;

expanding the middle portion of the implant outwardly in a radial direction to conform the shape of the implant to the shape of the space from which the disk has been removed;

injecting cancellous bone chips into the space between the vertebrae medial to the implant; and applying a physiologically compatible adhesive over the cancellous bone chips medial to the disk implant to close off the opening into the space from which the disk has been removed.

4. The method of claim 3 wherein expansion is accomplished by unwinding a plurality of spring-tensioned members comprising the middle portion of the implant, each of the members being mounted on and wound around a common longitudinal axis.

5. The method of claim 3 wherein expansion is accomplished by rotating a central rod, causing first and second end caps having holes therethrough for receiving the rod to move closer together to force hinged members comprising the middle portion of the implant radially outwardly.

6. The method of claim 1 wherein expansion is accomplished by unwinding a plurality of spring-tensioned members comprising the intermediate portion of the implant, each of the members being mounted on and wound around a common longitudinal axis.

7. The method of claim 1 wherein rotation of the central rod causes first and second end caps having holes therethrough for receiving the central rod and comprising the ends of the implant to move closer together to force hinged members comprising the intermediate portion of the implant radially outwardly.

8. The method of claim 1 further comprising injecting cancellous bone chips into the disk space medial to the implant.

9. A method of maintaining the space between two adjacent vertebrae of a patient after removal of a portion of the disk from therebetween comprising the steps of:

inserting an elongate implant into the space between two vertebrae after removal of a portion of the disk therefrom, the implant having a length which approximates the anterior-posterior dimension of the body of the vertebrae and a vertical dimension small enough to allow the insertion of the implant;

expanding the implant radially outwardly in the portion intermediate the ends thereof by rotating a central rod, causing first and second end caps having holes therethrough for receiving the rod to move closer together to force hinged members comprising the intermediate portion of the implant radially outwardly, to conform the shape of the implant to the shape of the anatomical region of the disk space into which the implant is inserted; and preventing the reversal of the outward radial expansion of the intermediate portion of the implant.

10. A method of stabilizing the spine of a patient comprising the steps of:

removing a portion of an intervertebral disk of the patient;

inserting an elongate implant into the space between the vertebrae from which the portion of the intervertebral disk has been removed and off center relative to the bodies of the adjacent vertebrae, the implant having a length which approximates the anterior-posterior dimension of the bodies of the vertebrae and a vertical dimension small enough to allow insertion of the implant through the gap between the vertebrae and adjacent the dorsal spine thereof;

expanding the middle portion of the implant outwardly in a radial direction to conform the shape of the implant to the shape of the space from which the portion of the intervertebral disk was removed; and injecting cancellous bone chips into the space between the vertebrae and medial to the implant.

11. The method of claim 10 further comprising applying a physiologically compatible adhesive over the cancellous bone chips to close off the gap through which the implant was inserted.

* * * * *